Figure 1:
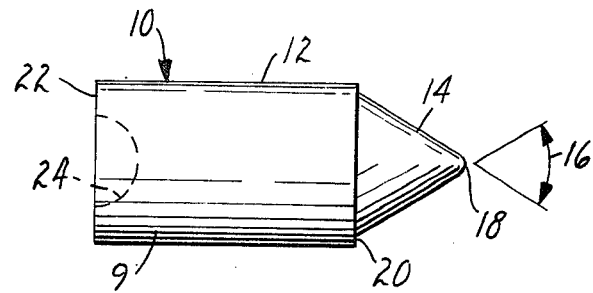

United States Patent [19]

Drake, Jr. et al.

[11] 4,326,524
[45] Apr. 27, 1982

[54] SOLID DOSE BALLISTIC PROJECTILE

[75] Inventors: James F. Drake, Jr., Minneapolis; G. Phillip Rambosek, Shafer Township, Chisago County, both of Minn.

[73] Assignee: Minnesota Mining and Manufacturing Company, St. Paul, Minn.

[21] Appl. No.: 192,297

[22] Filed: Sep. 30, 1980

[51] Int. Cl.$^3$ .............................................. A61M 7/00

[52] U.S. Cl. ..................................... 128/260; 128/217
[58] Field of Search ............... 128/260, 264, 268, 217; 424/19, 21, 22

[56] References Cited

U.S. PATENT DOCUMENTS

| | | | |
|---|---|---|---|
| 2,574,597 | 11/1951 | Salvin et al. | 8/79 |
| 3,166,476 | 1/1965 | Lowery | 167/82 |
| 3,362,880 | 1/1968 | Jeffries | 167/82 |
| 3,518,344 | 6/1970 | Welsh et al. | 424/44 |
| 3,619,292 | 11/1971 | Broullard | 127/29 |
| 3,622,677 | 11/1971 | Short et al. | 424/361 |
| 3,629,393 | 12/1971 | Nakamoto et al. | 424/22 |
| 3,632,739 | 1/1972 | Kornblum | 424/19 |
| 3,690,034 | 9/1972 | Knapp | 47/57.6 |
| 3,773,920 | 11/1973 | Nakamoto et al. | 424/19 |
| 3,774,607 | 11/1973 | Schmitz | 128/264 |
| 3,800,038 | 3/1974 | Rudel | 128/264 |
| 3,948,263 | 4/1976 | Drake et al. | 128/260 |
| 3,982,536 | 9/1976 | Krogseng | 128/260 |
| 3,991,750 | 11/1976 | Vickery | 128/260 |
| 4,096,239 | 6/1978 | Katz et al. | 128/260 |

OTHER PUBLICATIONS

"Ballistic Delivery of Biological Reagents", Prepared for Emergency Programs, USDA (Contract 12-16-14-0-213-91). Baldwin et al., 1973.

*Primary Examiner*—Robert W. Michell
*Assistant Examiner*—T. J. Wallen
*Attorney, Agent, or Firm*—Cruzan Alexander; Donald M. Sell; Jennie G. Boeder

[57] ABSTRACT

A solid dose ballistic projectile formed entirely of a cohesive mixture comprising biologically active material, in the form of grindable solid particles having an average diameter between about 7 and 25 micrometers, and biologically inert binder, and capable of withstanding the stresses imparted thereon when the projectile is propelled ballistically from a barrel and implanted in the flesh of a living animal.

18 Claims, 3 Drawing Figures

SOLID DOSE BALLISTIC PROJECTILE

FIELD OF THE INVENTION

The present invention relates to ballistic projectiles having a unique composition, and a unique method of manufacturing these projectiles. The projectiles of the present invention have physical characteristics which enable them to withstand the stresses of ballistic propulsion and implantation without disintegrating, even though they are made entirely of a mixture comprising biologically active material, in the form of grindable solid particles and biologically inert binder. The ballistic projectiles may comprise up to 95 percent by weight of medicament, including a friable crystalline medicament, while still remaining stress resistant.

BACKGROUND OF THE INVENTION

Ballistic projectiles containing biologically active materials for implantation into living animal bodies have been disclosed in U.S. Pat. No. 3,948,263 issued Apr. 6, 1976, and U.S. Pat. No. 3,982,536 issued Sept. 28, 1976. These implants generally comprise a non-lethal polymeric projectile having an interior cavity containing biologically active material, although, it is shown in U.S. Pat. No. 3,948,263, that biologically active material may be dispersed throughout the body of the projectile. Generally the implants of the prior art are capable of carrying about 30–35 percent by weight, and normally no more than 50 percent by weight of active medicament. Due to the limited amount of medicament that can be carried by these projectiles, it is necessary, particularly with antibiotic treatments, to use multiple ballistic implants to attain the proper dosage for an animal weighing, for example, 200 to 500 kg. While multiple ballistic implantations generally pose little risk to the health of the target animal and are not stressful to the animal, the use of multiple implants is inconvenient and may be impossible with free-ranging animals. Thus, it would be advantageous to provide the proper dosage with fewer, and in some cases only one, ballistic projectile.

SUMMARY

The present invention provides a solid dose ballistic projectile shaped for penetrating the epidermal layer of a living animal and lodging totally within the tissues of the animal, which is capable of releasing biologically active material into the tissues of the animal when lodged therein. "Solid dose" refers to the fact that the body of the projectile is made entirely of a mixture comprising biologically active material and inert binder, with no polymeric exterior casing. The projectiles of the present invention comprise in a major portion a body consisting essentially of a cohesive mixture of from about 70 to 95 weight percent grindable solid particles, at least about 90 weight percent of these particles having an average diameter between about 7 and 25 micrometers, and at least a biologically effective amount of these particles comprising a biologically active material, and from about 5 to 30 weight percent of a biologically inert, cohesive binder adhered to said particles. "Grindable" refers to the fact that the solid particles can be reduced in particle size by attrition in a ball mill at room temperature. The grindable solid particles are less compressible than the binder. The body is capable of providing structural integrity to the projectile when it is ballistically propelled at a muzzle velocity of up to 1,400 ft/sec. (475 m/sec) and implanted within the tissues of living animal.

Due to the unique composition of the projectiles of the present invention and the unique method of making them, no projectile shaped polymeric exterior casing in which to house the medicament is employed, thus allowing the projectiles of the present invention to comprise and deliver more active medicament than conventional ballistically implantable projectiles. In addition, since the solid dose projectiles of the present invention require no exterior casing, which has conventionally been formed from plastics which are either soluble or insoluble in the animal body, they may be more compatible with the biological system of the animal. The projectiles of the present invention require no subsequent removal of, and pose no danger of infection from, such an exterior casing.

The projectiles of the present invention, even though formed entirely from a preferably uniform mixture comprising medicament and binder and having no supporting polymeric exterior casing, are capable of withstanding the stresses imparted by ballistic propulsion from a gun barrel and implantation in the flesh of a living animal. The ballistic projectiles are capable of comprising up to 95 percent by weight solid particulate active medicament ingredient, including a friable crystalline one, without any resultant loss of ability to withstand the above mentioned stresses. The ability of the projectile to withstand such stresses is due to the projectile composition, including the particle size of the medicament, and in preferred embodiments, to both the shape of the projectile and the method by which it is made.

The projectiles are preferably compression molded from a normally uniform mixture of from about 70 to 95 weight percent grindable solid particles, at least 90 percent of which have an average diameter of about 7 to 25 micrometers, and wherein at least a biologically effective amount of the particles are biologically active material, and from about 5 to 30 weight percent of a biologically inert, cohesive binder. The method described above of molding a uniform mixture comprising very small (average diameter 7 to 25 micrometers) particles of solid medicament, provides ballistic projectiles which are essentially free of stress zones.

BRIEF DESCRIPTION OF THE DRAWINGS

FIG. 1 is side view of a first embodiment of a projectile according to the present invention.

FIG. 2 is a cross-sectional view of an alternative embodiment of a projectile of the present invention having a cavity adopted to carry additional biologically active material therein.

FIG. 3 is a side view of still another embodiment of a projectile according to the present invention.

DETAILED DESCRIPTION

The mixture from which the ballistic projectiles of the present invention are made consists essentially of about 70 to 95 weight percent grindable solid particles, most of which are very small (the average diameter being 7–25 micrometers) and about 5 to 30 weight percent binder. The solid particulate material may comprise adjuvants conventionally employed in preparing tablets by direct compression, such as lubricants, disintegrants, fillers, and the like. In addition, adjuvants of the type described above which are not in the form of grindable solid particulates may be added to the mixture as long as they do not comprise more than about 15 percent by weight of the mixture.

Useful grindable solid particulate biologically active materials include vaccines or bacterins; growth promoters such as hormones, minerals or vitamins; antibiotics, antigens, anthelmintics, or other medicinal drugs; and tranquilizers. The ballistic projectiles of the present invention are particularly useful in the administration of crystalline medicaments such as penicillins, both the acid and free base forms of the animal dewormer, Levamisole ® (a registered trademark of Cyanamid Corp.), tetracycline HCL and the free base, and erythromycin.

The amount of biologically active material present in the mixture and consequently present in the resultant ballistic projectile, can be up to about 95 percent by weight. It is preferred, particularly where the biologically active material is an antibiotic, that the mixture comprise at least about 70 weight percent of the solid particulate material as biologically active ingredient.

Suitable binders for inclusion in the mixture are biologically inert, cohesive materials having characteristics which enable them to impart compressibility to the mixture. Preferably the binder is a thermoplastic material. Moreover, the binder must be cohesive, that is, it must adhere to the solid particulate material and provide the compressible mixture with a degree of cohesiveness. The binder may have the additional feature of acting as a disintegrant. By proper selection of the binder, the disintegration rate can be controlled to supply the biologically active ingredient in a sustained release or in a quick release manner. The binder may also be chosen to be specific to certain body fluids and tissues, to supply biologically active materials to a localized area.

Binders which have the above described characteristics and which enable quick release of the medicament include such water soluble materials as hydroxypropylcellulose, hydroxypropylmethylcellulose, methylcellulose, sodium carboxymethyl cellulose, polyvinyl alcohol, polyvinyl pyrrolidone, gum arabic, etc. Hydroxypropylcellulose is a particularly preferred binder due to its compatibility with biological systems and its adhesive characteristics.

Binders which have the required characteristics and are suitable for use in sustained release formulations include such nonpolar-solvent soluble materials as polylactic acids and polyamides, such as polyglycine.

It is to be appreciated that by mixing sustained release and quick release binders, a wide range of dissolution rates can be achieved.

As mentioned hereinabove, the amount of binder present in the mixture and the resultant ballistic projectile is between about 5 and 30 percent by weight. Most preferably, in order to provide projectiles capable of delivering large doses of biologically active material, binder is present in a range of from 5 to 10 percent by weight.

The inclusion of lubricants in the mixture aids the ability of the mixture to flow into the dies of the molding machinery, and provides both surface lubrication and compression lubrication during compression molding. Suitable lubricants include powdered talc, magnesium stearate, carbowax and calcium stearate. Calcium stearate is preferred. The lubricant generally is added in an amount ranging up to about 5 percent by weight of the total formulation. At least about 2–3 percent by weight of the lubricant is preferred to assure that the molded projectile is easily released from the mold.

Preferred disintegrants for providing quick release of medicament include hydroxypropyl starch, available as Prima Gel® (a registered trademark of Edward Mendall, Inc.), calcium alginate, available as Kelset® (a registered trademark of Kelco Corp.), and sodium alginate. It has been found that about 3–4 percent by weight Prima Gel® or Kelset° enables release of even less soluble medicaments, such as procaine penicillin, in less than one hour. It is to be appreciated that by using different amounts and types of disintegrants and different types of biologically active ingredient a wide range of dissolution rates can be achieved.

Biologically inert filler material may be included in the mixture, particularly when the biologically active ingredient is a more potent medicament such as a soieriod. Exemplary grindable particulate materials which find use as fillers include calcium carbonate, crystalline lactose and sodium chloride. Solid particulate filler may be present in a concentration of up to about 30 percent by weight of the total solid particulate material.

It was not appreciated prior to applicants' invention that projectiles comprising up to 95 percent of a medicament, including a friable crystalline medicament, and capable of withstanding the stresses of ballistic propulsion and implantation could be manufactured. The prior art relating to both ballistic implants and shaped medicament tablets neither taught nor suggested that such high dose ballistic projectiles could be provided by compression molding a cohesive mixture of very small particles of the ingredient to be administered (average diameter of 7–25 micrometers) and the cohesive binder material. While U.S. Pat. No. 3,948,263, entitled "Ballistic Animal Implant", indicates that medicament particles may be dispersed throughout the body of the projectile, it in no way teaches a ballistic implant comprising up to 95 percent by weight medicament. In addition, the tablet manufacturing art does not recommend the use of medicament particles having a diameter much less than 50 μm. In fact, when the conventional methods of manufacturing shaped medicament tablets, as shown in U.S. Pat. Nos. 3,773,920; 3,622,677; and 3,629,393 were used to prepare a ballistic projectile of the present invention (comprising 90 percent by weight crystalline Levamisol® having an average diameter of about 100 μm, gum arabic and carbowax 400) it was found that the stresses imparted by ballistic propulsion resulted in the complete disintegration of the projectile as it left the gun barrel. Applicants' solved this problem by using a particle size below that recommended in the tabletting art, i.e., an average diameter of 7–25 μm, to produce their high dose projectiles capable of withstanding the forces of ballistic propulsion and implantation.

A preferred method of preparing the mixture of solid particulate material and binder is to apply the binder to the small solid particles by spray drying or freeze drying techniques. However, other means of providing the solid particles with a thin, more or less uniform coating of binder are contemplated. The procedure for applying the binder by means of spray drying is well known and is generally as follows: The binder is dissolved in a solvent in which the solid particulate material is insoluble. An amount of fine solid particles, i.e., have an average diameter of 7–25 micrometers, of the ingredient to be administered is dispersed in the binder solution. The amount of fine particles can be as much as about nineteen times the weight of the binder material dissolved in the binder solution, in order that the resultant projectiles can comprise up to 95 percent by weight of particulate ingredient. The slurry of fine particles in binder solution is atomized to produce finely-divided droplets of the slurry. The finely-divided liquid particles are then dried in a stream of heated air. Spray driers equipped with a centrifugal atomizing wheel and a heating chamber, such as a "Niro Atomizer" available from Niro Atomizer, Inc., are particularly useful for the above procedure. A cyclone separator may be used to recover the spray dried powder. The resultant spray-dried particles are less than 50 μm in diameter, with an average diameter of 15-20 μm, as observed by microscopic measurement.

The procedure for applying binder to the fine solid particles by means of freeze-drying is known and is as follows: The binder is dissolved in a solvent in which the solid particulate material is insoluble. An amount of fine particles (average diameter 7-25 μm) of up to nineteen times the weight of the binder material is dispersed in the binder solution. The resultant slurry is freeze-dried, broken-up, and screened to sub 50 μm in diameter sized particles.

Regardless of whether the spray drying or freeze drying technique is employed, the ballistic projectiles are preferably manufactured by pouring the mixture comprising uniformly small (below about 50 μm and preferably having an average diameter of 15-20 μm) binder coated particles, into a pill press and applying compacting pressure. A good quality non-frangible ballistic projectile results when 900 kg is applied for 5 seconds to a mold filled with about 0.5 gms of a uniform mixture of 95 parts by weight solid particles comprising 90 parts by weight sodium penicillin G freeze-dried with 10 parts hydroxypropylcellulose, and 5 parts by weight powdered calcium stearate. As is well known in the art, other projectile compositions may require different pressure and time regimes to produce good quality projectiles. Although the tablets produced by this method are hard and nonfriable they can be made to possess acceptable disintegration characteristics by proper choice of binder, disintegrant and compacting pressure.

The solid dose ballistic projectile of the present invention are preferably molded so that they have an elongate body portion with a central axis adapted for close fitting engagement with the inner surface of the bore of a barrel from which the projectile is propelled (e.g. such as the barrel of a compressed gas powered device), and a generally conical nose portion coaxial with the body portion. The conical nose portion preferably has a small radius on its apex.

Body portions of from 4.5 mm to 7.6 mm in diameter are most suitable, with body portions of 6.35 mm in diameter being preferred. For some limited applications of shallow implantation, body portions of up to 11.4 mm may also be suitable.

Preferably the conical nose portion has a base diameter smaller than the diameter of the body, so as to provide a slight shoulder where the base of the nose meets the body. The shoulder has been found useful in the production of stress relieved projectiles which will not crack when subjected to ballistic propulsion and implantation.

Preferably also, the projectile has a concave surface portion at its end opposite the nose portion, which concave surface portion is provided by the body. The concave surface produces much greater accuracy of flight for the projectile than does a flat end, presumably because it restricts tipping forces at the edge of the projectile due to escaping gas as the projectile exits from a barrel, and is particularly useful in obtaining accuracy for uniform mass projectiles.

Referring now to the drawings, there is shown in FIG. 1 a projectile according to the present invention generally designated by the numeral 10 and made entirely of a uniform mixture 9 of solid particles and binder. The projectile 10 comprises an elongate body portion 12 having a central axis and a cylindrical outer surface 6.35 mm in diameter. The body portion 12 is adapted to fit closely into the inner surface of a barrel from which the projectile is propelled as by being deformed into rifling in the barrel. Also the projectile includes a conical tip portion 14 coaxial with the body portion 12. The base of the tip portion 14 has a cross sectional area of 6.0 mm. Surrounding the base of the tip 14, between the outermost edge of the base and the outermost edge of the body 12 is a shoulder 20, which has a width of 0.18 mm. The conical tip portion 14 has an apex angle 16 of 60 degrees and has a 0.40 mm radius on its apex or terminal end surface 18, the center of which radius is on the axis of the tip portion 14. As illustrated the tablet is shaped to provide a concave surface portion 24 at the end surface 22 of the tablet.

Figure 2:
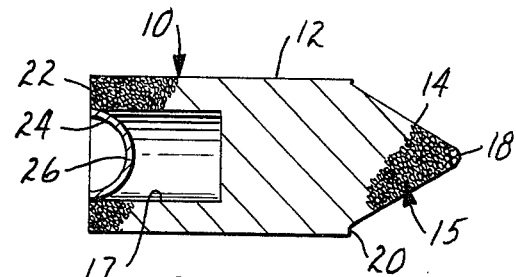

FIG. 2 shows a projectile 10 having an elongate body portion 12 and a conical tip portion 14, made entirely from a uniform mixture of solid particles 15, including the biologically active ingredient to be administered, and binder. The cavity 17 provided is optional. Where the cavity 17 is included, additional biologically active materials can be included therein so as to provide a "dual load" projectile. These additional materials may be the same as or different from the biologically active materials dispersed throughout the body of the projectile. These additional materials can be in the form of discrete solid particles, a solid block or plug, or a liquid. When the additional material is in the form of discrete solid particles, the particles may be suspended in a release sustaining matrix.

Any additionally included material may be sealed in cavity 17 by sealing means 26 positioned at the open end of the cavity. Sealing means 26 may be a microporous membrane which physically seals the biologically active material in the cavity 17 while allowing the passage of the material in response to a concentration or pressure gradient across the membrane, or may be a cap made of a soluble material which will dissolve in the animal body after being implanted and expose the biologically active material to the animal body fluid. Alternatively, the sealing means can be removably fastened to the projectile 10 in which case it can be removed prior to launching or can be constructed to separate from the projectile during launching, in flight, or at impact prior to entering the animal body.

The cavity 17 illustrated in FIG. 2 is cylindrical in nature, opening at the base and defined by annular projectile walls. However, other recesses or cavities which vary as to location or shape can be utilized with advantage. Moreover, the cavities need not be provided with an opening at the base of the projectile and may extend traversely of the projectile with access at the sides or other portion of the projectile.

The projectile 10 is provided at its end portion 22 with a concave surface portion 24. The concave surface portion may be formed from the material making up the projectile body, from additional biologically active material in cavity 17, or from sealing means 26.

Figure 3:
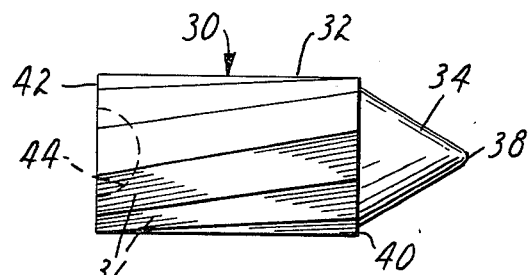

FIG. 3 illustrates an alternate embodiment of a projectile according to the present invention designated by the numeral 30. Like the projectile 10 of FIG. 1, the projectile 30 has a conical tip portion 34, an elongate body portion 32, a radiused apex or tip surface 38, and a shoulder 40 surrounding the base of the tip 34, which are respectively shaped like the tip portion 14, the tip surface 18, and the shoulder 20 of the projectile 10. The body portion 32 of the projectile 30, however, is not cylindrical on its outer surface but instead has ten flatted surface portions 36 of equal width around its periphery, which flatted surface portions 36 are evenly twisted about the axis of the projectile 30. These flatted surface portions 36 are adapted to fit closely within mating twisted flatted surfaces on the inner surface of a barrel from which the projectile 30 is to be propelled to provide a desired rotation during flight of the projectile. The projectile 30 is provided at its end surface 42 with a concave surface portion 44.

The invention can be further illustrated by reference to the following examples.

EXAMPLE 1

Fast release, sodium penicillin G ballistic projectiles having a shape similar to that shown in FIG. 3, were prepared by the following method. In 1000 parts/wt dichloromethane was dissolved 10 parts by weight of hydroxypropylcellulose. Next, 90 parts by weight of sodium penicillin G crystals, which had been passed through a No. 325 U.S. Sieve Series (44 micron opening) to break up the crystals into particles having a 15–20 $\mu$m average diameter, was dispersed into the cellulose solution. The slurry was spray dried using a spray drier equipped with a centrifugal atomizing wheel using an air turbine drive with a velocity of about 40,000 rpm. The heated chamber of the spray drier was maintained at 95° C. and the outlet temperature was about 50° C. The slurry was introduced to the atomizing wheel using a pump which maintained a flow rate of ~45 g/min. A cyclone separator was used to recover the spray dried powder from the exiting air/solvent stream. The spray dried material was sealed in moisture tight containers and frozen for storage.

A portion of the hydroxypropylcellulose coated penicillin was taken out of storage and screened through a 325 mesh screen to break up the agglomerates into spray dried particles 15–20 μm in diameter. A directly compressible formulation was prepared by dry mixing 95 parts by weight binder coated particles with 5 parts by weight powdered calcium stearate.

Solid dose ballistic tablets were compression molded to a shape similar to that shown in FIG. 3 by applying about 900 kg compacting pressure for about 5 seconds. Good quality, hard, non-frangible ballistic projectiles resulted.

Twelve 0.5 gram projectiles comprising 0.45 gm of sodium penicillin G were implanted in a 200 kg bovine suffering from respiratory ailment. All of the projectiles were propelled from the gun and into the animal in one piece without disintegrating. Six projectiles each day for two successive days were implanted. On the third day, the animal had fully recovered from the respiratory ailment.

To treat the same animal with the same dosage of sodium penicillin G using non-solid dose loaded ballistic projectiles, such as those disclosed in U.S. Pat. No. 3,948,263, would require 18 projectiles per day.

EXAMPLE 2

Tetracycline HCl projectiles having a shape similar to that shown in FIG. 3, were prepared by the following method. To 95 gms tetracycline HCl crystals which had been passed through a 325 mesh sieve so that they have an average diameter of 15–20 μl m, was added 5 gms hydroxypropylcellulose dissolved in a minimum amount of water. The slurry was stirred well to insure good wetting and coating of the crystals with the binder. The resultant slurry was freeze dried in a "Virtis" freeze-drier available from Virtis, Inc.

A portion of the freeze dried particles were broken-up and screened to assure sub 50 μm size. 95 parts by weight of the freeze dried particles were dry blended with 5 parts by weight of the die lubricant, powdered calcium stearate. This material was compression molded into 0.5 gm tablets having a shape similar to that shown in FIG. 3, using 900 kg compacting pressure held for 5 seconds. Good quality, hard, nonfrangible ballistic projectiles resulted.

The projectiles were propelled from an air gun into a gel material (90 percent by weight mineral oil and 10 percent by weight Shell Kraton 101), which has physical characteristics similar to animal muscle, with no apparent disintegration.

We claim:

1. A solid dose ballistic projectile shaped for penetrating the epidermal layer of a living animal and lodging totally within the tissues of the animal and capable of releasing biologically active ingredient into said tissue of said animal when lodged therein, the projectile comprising in a major portion a body consisting essentially of a uniform cohesive mixture of from about 70 to 95 weight percent of grindable solid particles, at least about 90 weight percent of said particles having an average diameter between about 7 and 25 micrometers, and at least a biologically effective amount of said particles comprising biologically active material, and from about 5 to 30 weight percent of a biologically inert, cohesive binder adhered to said particles, said binder being more compressible than said grindable solid particles, and said body being capable of providing structural integrity to said projectile when ballistically propelled at a muzzle velocity of up to about 475 m/sec and implanted within said tissues of said animal.

2. The solid dose ballistic projectile of claim 1 wherein said grindable solid particles comprise 100 percent by weight of said biologically active material.

3. The solid dose ballistic projectile of claim 1 wherein said biologically active material is selected from the group consisting of vaccines, bacterins, hormones, minerals, vitamins, antibiotics, antigens, anthelmintics, medicinal drugs, and tranquilizers.

4. The solid dose ballistic projectile of claim 1 wherein said biologically active material is a crystalline medicament selected from the group consisting of penicillins, tetracycline HCl, and erythromycin.

5. The solid dose ballistic projectile of claim 1 wherein said biologically inert binder is selected from the group consisting of hydroxypropylcellulose, hydroxypropylmethylcellulose, methylcellulose, sodium carboxypropylmethyl cellulose, polyvinyl alcohol, polyvinyl pyrrolidene, gum arabic, polylactic acids and polyamides.

6. The solid dose ballistic projectile of claim 1 wherein said grindable solid particles also comprise adjuvants selected from the group consisting of lubricants, disintegrants, and fillers.

7. The solid dose ballistic projectile of claim 6 wherein said adjuvant is a lubricant selected from the group consisting of talc, magnesium stearate, calcium stearate, and carbowax.

8. The solid dose ballistic projectile of claim 7 wherein said lubricant comprises up to about 5 percent by weight of said uniform cohesive mixture.

9. The solid dose ballistic projectile of claim 6 wherein said adjuvant is a disintegrant selected from the group consisting of hydroxypropyl starch, calcium alginate and sodium alginate.

10. The solid dose ballistic projectile of claim 6 wherein said adjuvant is a filler selected from the group consisting of sodium chloride, calcium carbonate, and crystalline lactose.

11. The solid dose ballistic projectile of claim 10 wherein said filler comprises up to about 30 percent by weight of said solid particles.

12. A method of manufacturing the solid dose ballistic projectile of claim 1 comprising compressing in a pill press said uniform cohesive mixture of said grindable solid particles, and said binder, said uniform cohesive mixture comprising said solid particles coated with a thin layer of said binder, said binder coated solid particles having an average diameter of less than 50 micrometers.

13. The method of claim 12 wherein said binder coating is applied to said grindable solid particles by spray or freeze drying techniques.

14. A ballistic projectile according to claim 1 wherein said projectile has an elongated body portion with a central axis, adapted for close fitting engagement with the inner surface of a barrel from which said projectile is to be propelled, and a generally conical nose portion with and projecting from one end of said body portion.

15. The ballistic projectile of claim 14 wherein the end of said body portion opposite said nose portion has a concave surface portion.

16. The ballistic projectile of claim 14 wherein said nose portion has a base diameter smaller than the diameter of said body portion so as to provide a slight shoulder where said base of said nose meets said body portion.

17. The ballistic projectile of claim 14 wherein said body portion has a cavity therein, said cavity capable of containing additional biologically active material.

18. A ballistic projectile according to claim 14 wherein said body portion has flatted surface portions of equal width around the periphery of said body portion, said flatted surface portions being evenly twisted about the axis of said tablet.

* * * * *